(12) United States Patent
Lee

(10) Patent No.: US 6,733,985 B1
(45) Date of Patent: May 11, 2004

(54) PREPARATION OF STABLE LIQUID AND DRIED SYNTHETIC PROTHROMBIN TIME REAGENTS

(75) Inventor: Ted C. K. Lee, Matawan, NJ (US)

(73) Assignee: International Technidyne Corporation, Edison, NJ (US)

( * ) Notice: Subject to any disclaimer, the term of this patent is extended or adjusted under 35 U.S.C. 154(b) by 458 days.

(21) Appl. No.: 09/314,841

(22) Filed: May 19, 1999

(51) Int. Cl.$^7$ ............... C12Q 1/56; C07C 229/00; A61K 31/197
(52) U.S. Cl. ............... 435/13; 562/576; 562/561; 536/65
(58) Field of Search ............... 435/13; 436/69, 436/71, 86; 530/363, 381; 536/46, 65; 554/79, 80; 562/576, 561; 560/19

(56) References Cited

U.S. PATENT DOCUMENTS

| | | | |
|---|---|---|---|
| 4,297,344 A | * 10/1981 | Schwinn et al. | |
| 4,756,884 A | * 7/1988 | Hillman et al. | ............... 422/73 |
| 5,314,695 A | 5/1994 | Brown | |
| 5,352,452 A | * 10/1994 | Kohmert et al. | |
| 5,358,853 A | 10/1994 | Butler et al. | |
| 5,418,141 A | 5/1995 | Zweig et al. | |
| 5,508,170 A | 4/1996 | Butler et al. | |
| 5,580,856 A | * 12/1996 | Prestrelski et al. | ............... 514/21 |
| 5,591,403 A | 1/1997 | Gavin et al. | |
| 5,625,036 A | 4/1997 | Hawkins et al. | |
| 5,730,969 A | * 3/1998 | Hora et al. | ............... 424/85.1 |
| 5,739,101 A | * 4/1998 | Roy et al. | |
| 5,858,724 A | 1/1999 | Novy, Jr. et al. | |

FOREIGN PATENT DOCUMENTS

| WO | WO98/48283 | 10/1998 |
|---|---|---|

OTHER PUBLICATIONS

Matsumoto Preventing freeze denature of milk or condensed milk–by adding an amino acid or its salt to the milk and storing in refrigerator Derwent–Acc–No.: 1981–24596D.*
Bach, Ronald R., "Initiation of Coagulation by Tissue Factor", CRC Critical Reviews in Biochemistry 1988; 23(4): pp. 339–368.
Nemerson, Yale, Tissue Factor and Hemostasis, *Blood* 71; pp. 1–8. (Jan. 1988).
J. Philpott et al., "A Very Mild Method Allowing the Encapsulation of Very High Amounts of Macromolecules into Very Large (1000 nm) Unilateral Lipsomes", Biochimica et Biophysica Acta; 734 137–143 (1983).
J.H. Lawson and K.G. Mann, J.Biol., Chem., 266, (17), 11317–11327. (Jun. 1991).
L.T. Mimms, et al., "Phospholipid Vesicle Formation and Transmembrane Protein Incorporation Using Octyl Glucoside", Biochemistry, 20,833–840 (1981).

R. Bach, et al., "Factor VII Bonding to Tissue Factor in Reconstituted Phospholipid Vesicles: Induction of Cooperativity by Phosphatidylserine", Biochemistry, 25, 4007–4020 (1986).
George J. Broze, Jr. et al, "Purification of Human Brain Tissue Factor*" The Journal of Biological Chemistry, vol. 260, No. 20, issue of Sep. 15, 1985, pp. 10917–10920.
Marcie C. Coots et al. "A Factor V Inhibitor: In Vitro Interference by Calcium", American Journal of Hematology, 1979,pp. 173–180.
Gregory Gregoriadis, Ph.D, Liposome Technology, vol. 1, Preparation of Liposomes. 1984, Chapter 11, pp. 139–161.
Freiburg Buchner et al. "Thrombosis Et Diathesis Haemorrhagica" 1965, pp. 393–395.
K.M. Brinkhous et al, "Thrombosis Et Diathesis Haemorrhagica", vol. XXI, 1969, pp. 547–560.
Ernest Jawetz, et al. "Review of Medical Microbiology", 1978, p. 86.
Jeffrey H. Lawson et al., "Cooperative Activation of Human Factor IX by the Human Extrinsic Pathway of Blood Coagulation*", The Journal of Biological Chemistry, vol. 266, Jun. 15, 1991, pp. 11317–11327.
R. Bruce Martin, "Introduction To Biophysical Chemistry", 1964, pp. 334–340.
Yale Nemerson, "The Phospholipid Requirement of Tissue Factor in Blood Coagulation", The Journal of Clinical Investigation, vol. 47, 1968, pp. 72–80.
R.R.C. New, "Liposomes A Practical Approach", Oxford University Press, 1990, pp. 17–18.
Linus Pauling, "College Chemistry, An Introduction Textbook Of General Chemistry", Third Edition, 1950, pp. 640–641.
J. Phillipot et al. A Very Mild Method Allowing The Encapsulation Of Very High Amounts Of Macromolecules Into Very Large (1000 nm) Unilamellar Liposomes, Biochimica et Biophysica Acta, 1983, pp. 137–143.
R. Bruce Martin, "Introduction To Biophysical Chemistry", 1964, p. 337.
Lawrence W. Powers, "Diagnostic Hematology Clinical and Technical Principles", 1989, p. 482.

* cited by examiner

Primary Examiner—Marjorie Moran
(74) Attorney, Agent, or Firm—Duane Morris LLP

(57) ABSTRACT

A reagent for determining prothrombin time (PT) including a recombinant protein tissue factor, a mixture of synthetic phospholipids, and a beta, gamma, or delta amino acid stabilizing compound is described for monitoring extrinsic blood coagulation activities. The source for the recombinant protein tissue factor is rabbit brain, and the phospholipids employed are palmitoyloleoylphosphatidylcholine (POPC) and palmitoyloleoylphosphatidylserine (POPS). The particular formulation buffer used to dilute the lipidated tissue factor provides a reagent that is optionally dried without lyophilization and remains stable for at least about 2 weeks at 37 C as either a liquid or a dried powder. A method for preparing the improved PT reagent and a method of using the reagent to analyze blood PT is also provided.

50 Claims, No Drawings

PREPARATION OF STABLE LIQUID AND DRIED SYNTHETIC PROTHROMBIN TIME REAGENTS

BACKGROUND OF THE INVENTION

1. Field of the Invention

The present invention relates to prothrombin time reagents for monitoring extrinsic blood coagulation activities, a method for preparing the reagent and a method for using the reagent. More particularly, the invention relates to a liquid and dried synthetic prothrombin time reagents, prepared from recombinant tissue factor and synthetic phospholipids, which are stable for an extended time and can be dried under ambient conditions.

2. Description of Related Art

Blood coagulation tests may be performed for a variety of purposes, including determination of the bleeding susceptibility of patients undergoing surgery and monitoring of patients undergoing anti-coagulation therapy for the prevention of blood clots. A number of coagulation tests presently are in use. One of these tests is the "prothrombin time" (PT) test. The PT test relies upon the induction of the extrinsic coagulation protease factor VIIa by thromboplastin in a blood sample to be tested. The extrinsic coagulation pathway results in the production of thrombin, a proteolytic enzyme that catalyzes the conversion of fibrinogen to fibrin, which is essential to the clotting process.

Thromboplastin, also known as tissue factor, is a membrane associated glycoprotein that forms a complex with blood coagulation factor VIIa. The complex formed enhances the proteolytic activity of factor VIIa. The functional activity of prothrombin depends on the presence of phospholipids (Bach, Ronald R., *Initiation of Coagulation by Tissue Factor*, CRC Critical Reviews in Biochemistry 1988; 23(4): pp.339–368). Once formed, the factor VIIa/tissue factor complex activates a series of specific enzymes that comprise the extrinsic and common pathways of the coagulation cascade, which ultimately lead to the formation of thrombin, fibrin, platelet activation, and finally clot formation (Nemerson, Yale, *Tissue Factor and Hemostasis*, Blood 1988; 71: pp. 1–8).

The prothrombin time (PT) test utilizes this series of enzymatic events in vitro under controlled conditions to diagnose dysfunctions or deficiencies in the blood coagulation system of patients. Other uses include the monitoring of patients undergoing anticoagulant therapy. The time period it takes for clot formation to occur is the Prothrombin Time, or PT value.

PT reagents are used to monitor the coagulation activities of the extrinsic pathway of plasma, including those from patients on Coumadin® therapy. For the PT test, a highly sensitive reagent with an International Sensitivity Index (ISI) of 1.0 is desired. With an ISI of 1.0, the calculation of the International Normalized Ratio (INR) of PT coagulation test is simplified.

A PT reagent must have the following characteristics: sensitivity to abnormal samples, a well-defined normal PT value for normal plasma, providing accurate and reproducible results, maintaining consistency from lot to lot, and stability for storage either in a liquid state or in a dried state and upon reconstitution.

Tissues of vertebrates that have been added to citrated plasma and then recalcified accelerate clotting time. The tissue constituent that activates the coagulation protease cascade is commonly referred to as thromboplastin, or tissue factor (TF). Tissue factors employed in the present PT tests contain crude tissue factor extracted from natural sources. Natural sources include rabbit brain, rabbit brain/lung tissue mixtures, human placenta, or ox brain. Each of these sources has problems associated with them. For example, rabbit brain thromboplastin shows some seasonal variability, it varies from lot to lot, and is in relatively short supply. Human tissue factor may contain HIV or other viral diseases. Ox brain provides values that are much longer than those observed when employing tissue factor from alternative sources. Crude tissue factor preparations from natural sources also contain other coagulation factors as contaminants. The contamination with coagulation factors results in coagulation factor assay curves that are less sensitive to factor-deficient plasmas.

Tissue factor requires phospholipids for functional activity. Phospholipids found in PT reagents generally are those that adhere to tissue factor when it is extracted from animal sources. For example, the extraction of rabbit brain results in the concurrent isolation of both tissue factor and naturally occurring phospholipids which are bound to the tissue factor in vivo and survive the extraction process. No additional lipids are usually added to such extracted tissue factor. As a result, the nature, quantity, and quality of the lipids employed in the PT reagent will therefore vary depending upon the starting tissues and the extraction process, and will lead to lot to lot inconsistencies. The DADE® thromboplastin reagents, Thromboplastin C, C+, and IS, available from Dade International, Inc. of Deerfield, Ill., are all based on extracts of acetone-dehydrated rabbit brain. Partially purified extracts are blended with specific mixtures of buffers and stabilizers. Since the partially purified tissue factor extract is not completely delipidated, the addition of lipids back into the extract is unnecessary. The nature and composition of the resulting lipids is not well defined and can vary from lot to lot.

Different thromboplastin preparations either improve or reduce discrimination between blood samples having different prothrombin times. Thromboplastins with greater discrimination are termed "more sensitive." The liquid phase sensitivity of a preparation is graded by use of the ISI value. The value is found by plotting on a logarithmic scale, the prothrombin time seen with a thromboplastin lot in question versus the prothrombin time values seen with a standardized lot of thromboplastin. The ISI value is the slope of the resulting line multiplied by the ISI of the reference thromboplastin. More sensitive thromboplastins have lower ISI numbers around 1.0, and less sensitive thromboplastins have higher ISI numbers, typically around 2 to 3.

In attempting to avoid the problems associated with tissue factor from natural sources, the use of recombinant tissue factor for use in a PT reagent is described in U.S. Pat. No. 5,625,036 titled "Preparation of Prothrombin Time Reagents from Recombinant Human Tissue Factor and purified Natural and Synthetic Phospholipids" issued Apr. 29, 1997 to P. L. Hawkins, et al., incorporated herein by reference. As described in the patent, human tissue factor is cloned and expressed in a number of organisms including *E. coli*. A portion of the cloned tissue factor is employed in the PT reagent without loss of functional activity, since most of the intracellular (cytoplasmic) domain of the cloned tissue factor can be truncated. The PT reagent includes recombinant tissue factor, phospholipids, either synthetic or natural, calcium ion, and a buffer composition. Well known cryopreservatives may also be added such as trehalose, maltose, and mannitol. Hawkins and other prior art preparation methods invariably require lyophilization or freeze-drying of the reagent for stability upon storage.

U.S. Pat. No. 5,314,695 titled "Tissue Factor Based Prothrombin Time Reagent" issued May 24, 1994 to S. M. Brown, incorporated herein by reference, relates to a tissue factor prothrombin time reagent in which the tissue factor is inserted into the phospholipid bilayer of liposomes or phospholipid vesicles. A buffer containing a cryopreservative and glycine preferably forms part of the formulation. Either natural tissue factor or recombinant tissue factor can be used. The formulation composition is adjusted to allow maximum coagulant activity and sensitivity to extrinsic coagulation factors. Brown's described preparation methods also require lyophilization.

U.S. Pat. No. 5,358,853 titled "Liquid Thromboplastin Reagent" issued Oct. 25, 1994 to J. R. Butler, et al., included herein by reference, describes a stable liquid thromboplastin reagent with a long shelf life which is prepared without lyophilization. However, the crude rabbit brain extract and unpurified phospholipids which comprise the liquid thromboplastin reagent of U.S. '853 could cause variability of the reagent with regard to the PT test.

U.S. Pat. No. 5,418,141 titled "Test Articles for Performing Dry Reagent Prothrombin Time Assays" issued May 23, 1995 to S. E. Zweig, et al., incorporated herein by reference, relates to test articles for performing dry reagent prothrombin time assays. The test articles comprise a solid phase membrane having dry, lyophilized thromboplastin immobilized therein. Coagulation neutral agents that facilitate rehydration of the dry thromboplastin are also provided on the solid phase membrane.

U.S. Pat. No. 5,508,170 titled "Liquid Thromboplastin Reagent" issued Apr. 16, 1996 to J. R. Butler, et al., incorporated herein by reference, relates to a stable liquid thromboplastin reagent which is derived from an acetone extract of rabbit brain tissue. The reagent described in U.S. Pat. No. 5,508,170 has a shelf life of greater than 16 months when packaged in a sealed container and is described as overcoming the inherent problems accompanying lyophilization, including: (1) variability in the filling of the vials before lyophilization; (2) shelf-to-shelf, and shelf positional differences in the lyophilization cycle (freezing and heating); (3) pipette errors associated with reconstitution and/or wrong volume additions when reconstituting the powder; and (4) water used to reconstitute may not be pure and/or may be contaminated with microorganisms. However the PT reagent sensitivity of the reagent described in U.S. Pat. No. 5,508,170 is substantially lower compared to recombinant tissue factor (e.g. approx. 2.0 Level III/I sensitivity compared to 4.0) because of the compositional variability of the rabbit brain tissue extract used in its preparation.

World Patent Application No. WO 98/48283 titled "Recombinant Rabbit Tissue Factor Based Prothrombin Time Reagent" published Oct. 29, 1998 to C. Brucato, et al., incorporated herein by reference, relates to liquid and lyophilized thromboplastin reagents derived from recombinant rabbit brain tissue factor where the removal of surfactant after mixing the surfactant-solubilized tissue factor with phospholipids is not necessary. However, no stability or shelf-life information with respect to the disclosed liquid thromboplastin reagent is provided.

Regarding another aspect of PT reagent formulation, a heterogeneous carbohydrate, Maltodextrin M-700 (a product of Grain Processing Corporation, Muscatine, Iowa), has been previously used (U.S. Pat. No. 5,591,403 titled "Portable Prothrombin Time Test Apparatus and Associated Method of Performing a Prothrombin Time Test" issued Jan. 7, 1997 to M. Gavin, et al., incorporated herein by reference). Maltodextrin and other polymeric carbohydrates are, in general, mixtures of several carbohydrates and may also contain aldehyde groups which could make an adduct with amino groups of proteins, such as tissue factor. Such heterogeneous carbohydrates may also be characterized by lot to lot variation, resulting in variation of performance of PT reagents formulated with such carbohydrates.

There remains a need therefore for a highly sensitive and consistent PT reagent that also remains stable either in the liquid stage or upon drying, but in either case without the complexity of lyophilization or impregnation into a membrane matrix, thereby rendering the PT reagent easier to manufacture, handle, transport, store, and use.

SUMMARY OF THE INVENTION

Briefly described, the invention comprises a PT reagent, a method of producing a PT reagent with a high degree of reproducibility for determining PT values, and a method of using the reagent. The inventive reagent is also highly stable upon either drying above 10° C. in air, nitrogen, or a vacuum, or upon exposure to air at elevated temperatures in the liquid state. The inventive reagent has a long shelf life at 20° C. in either the liquid or dried state, and remains stable at 37° C. for about 2 weeks or longer.

Recombinant tissue factor, preferably containing a portion derived from rabbit brain, is solubilized and mixed with a mixture of solubilized, synthetic phospholipids in an appropriate ratio in the presence of one or more substituted or unsubstituted beta, gamma, or delta amino acids as stabilizing compounds. Suitable synthetic phospholipids include palmitoyloleoylphosphatidylcholine and palmitoyloleoylphosphatidylserine. Suitable amino acid stabilizing compounds include beta alanine, gamma aminobutyric, and delta aminovaleric acid, etc. Other useful stabilizing compounds are illustrated in Table A. In a preferred embodiment, the phospholipids are solubilized in a suitable detergent such as is octylglucoside dissolved in a suitable buffer such as Hepes buffer,(4-(2-hydroxyethyl)-1-piperazineethanesulfonic acid) containing one or more of either beta alanine, gamma aminobutyric acid, or delta aminovaleric acid as the amino acid stabilizing compound. Other ancillary ingredients may be used, such as e.g., a salt such as sodium chloride(NaCl), an antioxidant such as BHT (butylated hydroxytoluene), a carrier protein such as bovine serum albumin (BSA), and a humectant such as sorbitol (D-glucitol). Upon solubilizing the components, the solution is subjected to dialysis.

A hydrophobic resin such as polystyrene divinylbenzene, polystyrene or polyacrylic resin, and the like, is optionally placed in the dialysis medium to increase dialysis efficiency. For example, Bio-Beads SM-2®, a polystyrene divinyl benzene has been reported to be especially effective; see e.g. J. Philippot, et al., "A Very Mild Method Allowing the Encapsulation of Very High Amounts of Macromolecules into Very Large (1000 nm) Unilamellar Lipsomes", Biochimica et Biophysica Acta; 734 137–143 (1983).

The dialysis medium comprises e.g. a buffer such as Hepes buffer, one or more of a beta, gamma, or delta amino acid stabilizing compounds, a salt such as sodium chloride, and a humectant such as sorbitol.

Upon completion of dialysis, the inventive composition is formulated and optionally dried above 10° C. in air, nitrogen or a vacuum in a relative humidity above about 2% RH.

Other combinations of temperature, gas composition, and humidity may be used provided that they allow the inventive composition to dry to the final desired moisture level, preferably about 2 to 10% moisture, in the desired time period. The dried materials are stored in a suitable container and are reconstituted with either water, plasma, blood, or the like; for use in coagulation-based assays when needed.

The liquid or reconstituted, air-dried reagent of the present invention is suitable for use in coagulation instruments such as the Fibrometer, MLA instrument of Medical Laboratory Automation Inc (Pleasantville, N.Y.), and the ACL instrument of Instrumentation Laboratories, Inc. (Lexington, Mass.).

DETAILED DESCRIPTION OF THE INVENTION

The prothrombin time reagent and methods of the present invention employ recombinant protein tissue factor, one or more synthetic phospholipids comprising e.g. palmitoyloleoylphosphatidylcholine (POPC) and palmitoyloleoylphosphatidylserine (POPS) and one or more beta, gamma or delta amino acid stabilizing agents for monitoring the activity of the extrinsic blood coagulation pathway.

In the present invention, the recombinant tissue factor is preferably combined with or lipidated by a mixture of two synthetic phospholipids. Preferably, recombinant tissue factor derived from rabbit brain is employed. Recombinant tissue factor (r-TF) derived from rabbit brain is available from commercial sources. For example, in the present invention, a suitable r-TF derived from rabbit brain is available as a clear solution from Pel Freeze, Inc. of Rogers, Ark.; and is characterized as an apoprotein consisting of a fusion molecule of approx 45 Kd, containing extracellular and transmembrane domains of tissue factor, plus an amino terminal leader sequence consisting of several domains which aid in expression and purification. U.S. Pat. No. 5,858,724 titled "Recombinant Rabbit Tissue Factor", issued Jan. 12, 1999 to R. E. Novy Jr., et al., contains a further description of a suitable r-TF and is hereby incorporated by reference. The tissue factor is solubilized in a suitable detergent, e.g. octylglucoside and then combined with or lipidated by a mixture of synthetic phospholipids. Preferably, the concentration of the r-TF for the reagent preparation is 200 to 250 μg/ml.

Synthetic phospholipids, which are conveniently obtained from the manufacturer in ampoule form, are dissolved in a detergent solution and mixed together in a suitable ratio for the present composition. The synthetic phospholipid combination utilized in the present invention are not found in naturally occurring phospholipid mixtures. Preferably, the synthetic lipids employed are 1-palmitoyl-2-oleoyl-phosphatidylcholine (POPC) and 1-palmitoyl-2-oleoyl-phosphatidylserine (POPS), and the like. POPC and POPS are further characterized in that they contain one double bond in their molecular structures and their phase transition temperature are −2 and 14° C. respectively (See e.g. "Thermotropic Phase Transitions of Pure Lipids in Model Membranes and Their Modifications by Membrane Proteins" J. R. Silvius, Lipid-Protein Interactions, J. Wiley & Sons, Inc., New York, 1982; and Lipid Thermotropic Phase Transition Database (LIPIDAT)—NIST Standard Reference Database 34). In a preferred embodiment, POPC and POPS are added in a molar ratio range of about 6:4 to 8:2 respectively, preferably about 7:3. The preferred synthetic lipids have been previously described by J. H. Lawson and K. G. Mann, J. Biol., Chem., 266, 11317 (1991). The advantage of utilizing synthetic phospholipids as opposed to natural phospholipids is that the composition of natural phospholipids is variable, depending upon the source. In contrast, the chemical composition of synthetic phospholipids is more defined and therefore more consistent.

POPC and POPS are available from a number of commercial sources, including e.g. Avanti Corporation (Alabaster, Ala.), sold under Catalog No. 850457 and 830034, respectively. The synthetic phospholipids are dissolved in a suitable detergent solution such as octylglucoside. Preferably, the phospholipids dissolved in the mixture have a concentration in the range of about 11 to 14 mM preferably in the range of about 12 to 13 mM.

The tissue factor, along with a suitable carrier protein, such as bovine serum albumin, is lipidated by the dissolved phospholipids by solubilizing in an aqueous solution of a suitable detergent. Octylglucoside (n-Octyl β-D-glucopyranoside) is preferred and is available from Sigma Chemical Co., Catalog No. O8001. Other detergents may be used provided the concentration of micelles or liposomes in the detergent is high enough to permit later dialysis of the solution. The concentration of the detergent, e.g. octylglucoside, is in the molar ratio of 15 to 65 mM with respect to the phospholipid, preferably in the molar ratio of 45 to 50 mM.

The amino acid stabilizer compound is represented by the following general formula I or a precursor thereof;

(I) 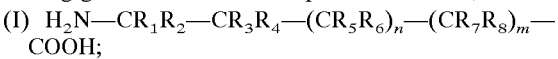
COOH;

wherein n represents 0 or 1; m represents 0 or 1; and $R_1$ and $R_2$ may be the same or different and represent a hydrogen atom, a hydroxyl group, an amino group, an alkyl group, an alkoxyl group, a thioether group, an aryl group, or a heterocyclic group; either substituted or unsubstituted; and $R_3$, $R_4$, $R_5$, $R_6$, $R_7$, and $R_8$ may be the same or different and represent a hydrogen atom, a hydroxyl group, an amino group, a carboxyl group, a carbonyl containing group, an alkyl group, an alkoxyl group, a thioether group, an aryl group, or a heterocyclic group; either substituted or unsubstituted.

Precursor compounds such as esters or salts are known in the art and are here defined as compounds that may form the inventive amino acid stabilizer compound in situ during the preparation or storage of the PT reagent. Such precursor compounds may be substituted in whole or in part for the free amino acid stabilizer compound described above.

Examples of suitable amino acid stabilizer compounds, also known as beta amino acids when n is 0 and m is 0, or gamma amino acids when n is 1 and m is 0, or delta amino acids when n is 1 and m is 1, are provided in Table A. Several inventive and comparative amino acid compounds were formulated to make PT reagents, and their effect on PT sensitivity (i.e. Level III/I ratio) was measured (see Examples 1 to 13 below). These experimental results are summarized in Table B. Satisfactory results mean that a Level III/I ratio of between 4.0 and 5.0 was obtained, while unsatisfactory results mean that a Level III/I ratio outside this range was obtained.

Beta alanine, gamma aminobutyric, and delta aminovaleric acid are especially preferred amino acid stabilizer compounds due to their low cost and ready availability. The inventive amino acid stabilizer compounds are added in the concentration range of about 0.1 to 10.0% (w/v), preferably in the range of about 1.0 to 5.0% (w/v), with an especially preferred range of about 1.5 to 2.5% (w/v). Suitable amino acid stabilizer compounds are also soluble or dispersible in the aqueous medium.

TABLE A

Examples of Inventive Amino Acid Stabilizer Compounds

| Name of compound | Structure |
|---|---|
| 1) Beta alanine | $H_2NCH_2CH_2COOH$ |
| 2) Gamma aminobutyric acid | $H_2NCH_2CH_2CH_2COOH$ |
| 3) 3-Amino butyric acid | $H_2NCH(CH_3)CH_2COOH$ |
| 4) 4-Amino-2-hydroxybutyric acid | $H_2NCH_2CH_2CH(OH)COOH$ |
| 5) 4-Amino-2-methoxybutyric acid | $H_2NCH_2CH_2CH(OCH_3)COOH$ |
| 6) 4-Amino-3-hydroxybutyric acid | $H_2NCH_2CH(OH)CH_2COOH$ |
| 7) 4-Amino-3-methoxybutyric acid | $H_2NCH_2CH(OCH_3)CH_2COOH$ |
| 8) 3-Amino-2-hydroxypropanoic acid | $H_2NCH_2CH(OH)COOH$ |
| 9) 3-Amino-2-methoxypropanoic acid | $H_2NCH_2CH(OCH_3)COOH$ |
| 10) 3-Amino-4-hydroxybutyric acid | $H_2NCH(CH_2OH)CH_2COOH$ |
| 11) 3-Amino-4-methoxybutyric acid | $H_2NCH(CH_2OCH_3)CH_2COOH$ |
| 12) 3-Amino-4,4,4-trifluorobutyric acid | $H_2NCH(CF_3)CH_2COOH$ |
| 13) 3-Amino-3-methylbutyric acid | $H_2NC(CH_3)_2CH_2COOH$ |
| 14) 3-Amino isobutyric acid | $H_2NCH_2CH(CH_3)COOH$ |
| 15) 3-Amino-3-phenylpropanoic acid | $H_2NCH(C_6H_5)CH_2COOH$ |
| 16) Delta aminovaleric acid | $H_2NCH_2CH_2CH_2CH_2COOH$ |

TABLE B

Inventive and Comparative Amino Acid Stabilizer Compounds and Clotting Time Ratio Test Results:

| Name of compound | Structure | Level III/I ratio test results |
|---|---|---|
| Beta alanine (inventive) | $H_2NCH_2CH_2COOH$ | Satisfactory |
| Gamma aminobutyric acid (inventive) | $H_2NCH_2CH_2CH_2COOH$ | Satisfactory |
| Delta aminovaleric acid (inventive) | $H_2NCH_2CH_2CH_2CH_2COOH$ | Satisfactory |
| Aspartic acid (comparative) | $H_2NCH(COOH)CH_2COOH$ | Unsatisfactory |
| Arginine (comparative) | $H_2NC(=NH)NHCH_2CH_2CH_2CH(NH_2)COOH$ | Unsatisfactory |
| Glycylglycine (comparative) | $H_2NCH_2C(=O)NHCH_2COOH$ | Unsatisfactory |
| ε-aminocaproic acid (comparative) | $H_2N(CH_2)_5COOH$ | Unsatisfactory |

Suitable carrier proteins function as a stabilizer for in vitro reactions, especially involving proteins. Suitable carrier proteins include BSA, ovalbumin, and gamma globulin and the like, and are used in a concentration of about 0.01 to 1.0% (by weight). Preferably BSA is used at about 0.3% and may be obtained from Sigma Chemical Co. (St. Louis, Mo.).

The inventive solution also optionally contains a suitable antioxidant, especially if air-drying is employed to prepare the PT reagent. Antioxidants prevent e.g. the oxidation of lipids to fatty acids. Suitable antioxidants include butylated hydroxytoluene (BHT), butylated hydroxyanisole (BHA), or Vitamin E and the like, in a concentration range of about 0.001 to 0.10% (by weight). Preferably, BHT is used at about 0.01% by weight.

In addition, the solution contains a suitable buffer such as Hepes, MOPS (4-Morpholinepropanesulfonic acid), TES (2-[[tris(hydroxymethyl)methyl]amino]-1-ethanesulfonic acid), DIPSO (3-[bis(2-hydroxyethyl)amino]-2-hydroxy-1-propanesulfonic acid), and the like, in a concentration range of 10 to 100 mM. Preferably the buffer used is Hepes at about 14 mM in concentration.

A salt is used such as sodium chloride, potassium chloride, and the like, in a concentration range of about 0.02 to 0.2 M. Sodium chloride is preferably used in a concentration amount of between about 30 mM and 60 mM.

A suitable amino acid chelating agent is optionally used such as L-serine, threonine, alpha alanine, and the like, in a concentration range of about 0.1 to 10% (by weight). Amino acid chelating agents can prevent precipitation by chelating metal ions that may be present in the composition as a result of the formulation process. Preferably L-serine is used at about 4 to 5% (by weight). Suitable amino acids are also employed during micelle or liposome formation along with recombinant rabbit brain tissue factor during the process of making the inventive composition such as beta alanine, glycine, alpha alanine, L-serine, and the like. Such amino acids are employed in a concentration of about 1 to 10% (by weight) with respect to the phospholipids. Preferably beta alanine or glycine is used in a concentration of about 4 to 6% (by weight).

One or more humectants are used such as glycerol (1,2,3-propanetriol), glycerol esters, sorbitol, ethylene glycol, propylene glycol, polyethylene glycol, and the like, in a total concentration range of about 1.0 to 10.0% (by weight). Preferably glycerol and sorbitol are used in a concentration range of about 0.1 to 0.5% (by weight) and about 2.0 to 7.0% (by weight), respectively when the invention reagent will be dried. A humectant, such as sorbitol, is added to the reagent mixture for stability and to provide tackiness or stickiness upon optional drying of the reagent. Although the mixture can be optionally dried to a powder form without a humectant, it has been found that the tackiness provided by a humectant is preferable when reconstituting the reagent. Moreover, the stickiness prevents the dried reagent from migrating within a test cuvette. Glycerol also imparts stickiness to the dried reagent, and is also preferably added as a moisture protectant to the solution when a dry reagent is desired.

An aldehyde free polymeric carbohydrate may be optionally used to adjust the sensitivity of the inventive PT reagent. Such a compound is defined as a polymeric carbohydrate which has no aldehyde group in its molecular structure. Preferably an aldehyde free synthetic polymeric carbohydrate is used which has a purity of greater than 90% (by weight) with respect to both molecular structure and molecular weight variation. Most preferably, gamma cyclodextrin (1297 MW) which contains 8D-glucopyranose units by alpha-(1–4) linkage is used in the inventive PT reagent; preferably at about 1% w/v in concentration on a diluted basis.

As discussed above, one or more synthetic lipids are dissolved in a suitable detergent solution and recombinant tissue factor is added followed by a carrier protein. The detergent can be removed by several methods known in the art to form a phospholipid tissue factor micelle (see e.g. L. T. Mimms, et al., "Phospholipid Vesicle Formation and Transmembrane Protein Incorporation Using Octyl Glucoside", Biochemistry, 20, 833–840 (1981), and R. Bach, et al., "Factor VII Bonding to Tissue Factor in Reconstituted Phospholipid Vesicles: Induction of Cooperativity by Phosphatidylserine", Biochemistry, 25, 4007–4020 (1986)). Suitable methods for detergent removal include dialysis, ultrafiltration, hydrophobic chromatography and the like.

In a preferred embodiment, the synthetic phospholipids, POPC and POPS, are dissolved in a detergent solution, in a molar ratio of 7 to 3 respectively, along with recombinant tissue factor and a beta or gamma amino acid stabilizer. The mixture is incubated at room temperature with gentle shaking for 60 minutes. The detergent in the mixture is then removed by dialysis.

In one preferred method, dialysis proceeds by placing the mixture in a dialysis bag and dialyzing at about 4° C. against one or more Hepes buffer solutions. Dialyzed material in Hepes buffer also preferably contains 5% beta alanine as the amino acid stabilizer, 2% sorbitol and 0.1M sodium chloride. In another preferred embodiment, two dialysis solutions are used wherein the first solution contains 5% glycine and the second solution contains 5% L-serine as the respective amino acid chelating agents. After dialysis, the dialyzed material is drained from the dialysis bag and collected in a sterile polypropylene tube.

The dialyzed mixture containing the lipidated tissue factor is then diluted with a formulation buffer, preferably including Hepes, one or more beta, gamma or delta amino acid stabilizing compounds; sodium chloride, L-serine, sorbitol, BSA, BHT, a suitable biocide, and a suitable calcium ion source.

Suitable ionizable calcium sources include e.g. calcium salts of gluconate, acetate, or chloride and the like in a preferred concentration of range of about 10 to 20 mM. Calcium ions are essential for the activity of calcium dependent coagulation factors, such as Factors II, VII, IX and X. Calcium gluconate is preferred as the calcium ion source, and is preferably added in about a 14 mM concentration.

Suitable biocides include e.g. phenol, and antibiotics such as penicillin or Kanamycin and the like which are added in an effective concentration range to inhibit biogrowth in the inventive composition. Phenol in the concentration range of 0.1 to 0.2% (by weight) is preferred.

If a dried material is desired, the formulated reagent is dried without lyophilization at a temperature above about 10° C. and a relative humidity of above about 2%. Preferably the material is air-dried at about 20° C. and about 5% relative humidity, to yield a highly stable prothrombin time test reagent. Upon reconstitution with water, the reagent is subjected to coagulation assays employing a traditional prothrombin time test method, using a Fibrometer.

Concerning the ISI value, the inventive reagent provides a value of 1.0±0.05 which greatly simplifies the calculation of the International Normalized Ratio (INR), as is apparent from the following formula for calculating the INR:

$$INR = (PT\ Ratio)^{ISI}$$

$$PT\ Ratio = \frac{PT\ patient}{mean\ normal\ PT}$$

The liquid or dried product of the present invention has an ISI value of substantially 1.0. An ISI value of 1.0 is preferred, since values reaching 2 or 3 indicate a less sensitive reagent.

The inventive reagent can be placed in a various coagulation instruments for testing. For example, the air-dried reagent is reconstituted and placed in a cuvette of the MLA instrument for assay purposes.

Thus, the highly sensitive reagent is optimized for long shelf life in either the liquid or dry state, without the need for lyophilization. If the material is dried, it is preferably air-dried under ambient conditions. Rehydration of the reagent is rapid, and the stickiness of the reagent prevents the reagent from moving within the chosen test device prior to reconstitution. The reagent is highly stable. The liquid or air-dried reagent, maintained at a temperature of 37° C., remains stable for at least about 2 weeks.

Examples 1 to 12 which follow will serve to further typify the nature of the invention. Example 13 illustrates clotting time test results for comparative amino acids described in Table A. Examples 1 to 13 should not be construed as a limitation on the scope thereof, which is defined solely by the appended claims.

While the invention has been described with reference to the preferred embodiments thereof, it will be appreciated by those of ordinary skill in the art that modifications can be made to the parts that comprise the invention without departing from the spirit and scope thereof.

EXAMPLE 1

Synthetic phospholipids, palmitoyloleoylphosphatidylcholine (POPC) and palmitoyloleoylphosphatidylserine (POPS), were dissolved at 45° C., respectively, in 600 mM octylglucoside (a detergent), 0.1 mg per ml butylated hydroxytoluene (BHT), 14 mM Hepes, 0.1 M sodium chloride, 5% beta alanine and 2% sorbitol, pH 7.4. The concentration of the dissolved phospholipids was 12.76 mM. These phospholipids were chosen based on the publication by J. H. Lawson and K. G. Mann (J. Biol. Chem., 266, 11317–11327 (1991), in which they demonstrated a successful lipidation of recombinant tissue factor. The dissolved phospholipids were mixed with a molar ratio of 7 to 3 (POPC:POPS) as described in the published procedure by R. Bach, R. Gentry, and Y. Nemerson (Biochemistry, 25, 4007–4020, (1986). Bovine serum albumin (BSA) and recombinant rabbit brain tissue factor were added to a concentration of 0.06 mg/ml and 39 $\mu$g/ml, respectively. The mixture was incubated at room temperature for one hour with gentle shaking. Additional bovine serum albumin was added to a concentration of 4.8 mg/ml. The mixture was then placed in a dialysis bag, and dialyzed at 4° C. against a buffer solution of 14 mM Hepes, 0.1 M sodium chloride, 5% beta alanine and 2% sorbitol, pH 7.4. The dialyzed lipidated tissue factor, was then drained from the dialysis bag. The lipidated tissue factor was diluted 100-fold with a formulation buffer, which is composed of 14 mM Hepes, 60 mM sodium chloride, 2% beta alanine, 4.5% L-serine, 7% sorbitol, 14 mM calcium gluconate, 0.3% BSA, 0.2% phenol and 0.01% BHT, pH 7.4. The formulated material was frozen at −70° C., and then thawed. The thawed formulated material was incubated at 25 and 37° C. for 4 weeks, The reagent was taken out from the incubation at weekly intervals and subjected to coagulation assay by traditional prothrombin time test method using a Fibrometer. The control plasma samples used for the assay were Level I (normal control) and Level III (abnormal control) of Ortho Diagnostics Corporation. (New Jersey). The Level III abnormal control plasma contains a reduced amount of coagulation factors representing the plasma of patients.

TABLE 1

| | | Clotting Times (Seconds) | | |
|---|---|---|---|---|
| Incubation days | Temp. (° C.) | Level I | Level III | III/I Ratio |
| 0 | 25 | 12.9 | 57.2 | 4.43 |
| 7 | 25 | 12.5 | 57.4 | 4.59 |
| 14 | 25 | 12.8 | 55.5 | 4.34 |
| 21 | 25 | 12.4 | 52.9 | 4.27 |
| 28 | 25 | 12.7 | 54.5 | 4.29 |
| 7 | 37 | 12.9 | 56.4 | 4.37 |
| 14 | 37 | 13.2 | 58.4 | 4.42 |
| 21 | 37 | 13.0 | 53.9 | 4.15 |
| 28 | 37 | 13.6 | 57.8 | 4.25 |

EXAMPLE 2

The lipidated, dialyzed tissue factor with beta alanine of Example 1 was diluted 100-fold with a formulation buffer, which is composed of 14 mM Hepes, 30 mM sodium chloride, 2% beta alanine, 4.5% L-serine, 7% sorbitol, 14 mM calcium gluconate, 0.3% BSA, 0.2% phenol, and 0.01% BHT. The formulated material was frozen at −70° C., and then thawed. The formulated material with freezing-thawing was incubated at 25 and 37° C. for 4 weeks. The reagents was taken out from the incubator at weekly intervals and subjected to coagulation assay by traditional prothrombin time test method.

TABLE 2

| | | Clotting Times (Seconds) | | |
|---|---|---|---|---|
| Incubation days | Temp. (° C.) | Level I | Level III | III/I Ratio |
| 0 | 25 | 13.0 | 53.2 | 4.09 |
| 7 | 25 | 12.4 | 51.9 | 4.19 |
| 14 | 25 | 12.5 | 51.9 | 4.15 |
| 21 | 25 | 12.4 | 51.7 | 4.17 |
| 28 | 25 | 11.8 | 51.1 | 4.33 |
| 7 | 37 | 12.5 | 53.9 | 4.31 |
| 14 | 37 | 12.5 | 51.9 | 4.15 |
| 21 | 37 | 12.9 | 55.0 | 4.26 |
| 28 | 37 | 12.8 | 53.3 | 4.16 |

EXAMPLE 3

Synthetic phospholipids, palmitoyloleoylphosphatidylcholine (POPC) and palmitoyloleoylphosphatidylserine (POPS), were dissolved at 45° C., respectively, in 600 mM octylglucoside (a detergent), 0.1 mg per ml butylated hydroxytoluene (BHT), 14 mM Hepes, 0.1 M sodium chloride, 5% L-alanine and 2% sorbitol, pH 7.4. The concentration of the dissolved phospholipids was 12.76 mM. The dissolved phospholipids were mixed with a ratio of 7 to 3. Bovine serum albumin and recombinant rabbit brain tissue factor were added to a concentration of 0.06 mg/ml and 39 µg/ml, respectively. The mixture was incubated at room temperature for one hour with gentle shaking. An additional bovine serum albumin was added to a concentration of 4.8 mg/ml. The mixture was then placed in a dialysis bag, and dialyzed at 4° C. against a buffer solution of 14 mM Hepes, 0.1 M sodium chloride, 5% L-alanine and 2% sorbitol, pH 7.4. The dialyzed mixture, lipidated tissue factor, was then drained from the dialysis bag. The lipidated tissue factor was diluted 100-fold with a formulation buffer, which is composed of 14 mM Hepes, 60 mM sodium chloride, 2% beta alanine, 4.5% L-serine, 7% sorbitol, 14 mM calcium gluconate, 0.3% BSA, 0.2% phenol and 0.01% BHT, pH 7.4. The formulated material was frozen at −70° C., and then thawed. The formulated material was subjected to prothrombin time clotting assay and stability studies as in the Example 1.

TABLE 3

| | | Clotting Times (Seconds) | | |
|---|---|---|---|---|
| Incubation days | Temp. (° C.) | Level I | Level III | III/I Ratio |
| 0 | 25 | 12.0 | 50.0 | 4.17 |
| 7 | 25 | 12.0 | 48.4 | 4.03 |
| 14 | 25 | 12.2 | 47.4 | 3.89 |
| 21 | 25 | 12.1 | 47.0 | 3.88 |
| 28 | 25 | 11.8 | 47.3 | 4.09 |
| 7 | 37 | 11.9 | 51.9 | 4.36 |
| 14 | 37 | 12.0 | 48.2 | 4.02 |
| 21 | 37 | 12.0 | 46.2 | 3.85 |
| 28 | 37 | 11.9 | 45.0 | 3.78 |

EXAMPLE 4

The lipidated, dialyzed tissue factor with beta alanine of Example 1 was diluted 100-fold with a formulation buffer, which is composed of 14 mM Hepes, 60 mM sodium chloride, 2% beta alanine, 4.5% L-serine, 9% sorbitol, 14 mM calcium gluconate, 0.3% BSA, 0.2% phenol, and 0.01% BHT. The formulated material was frozen at −70° C., and then thawed. The thawed material was incubated at 37° C. and assayed at weekly intervals by prothrombin time test method.

TABLE 4

| | | Clotting Times (Seconds) | | |
|---|---|---|---|---|
| Incubation days | Temp. (° C.) | Level I | Level III | III/I Ratio |
| 0 | 37 | 13.4 | 68.9 | 5.14 |
| 7 | 37 | 13.4 | 67.0 | 5.00 |
| 14 | 37 | 14.2 | 76.6 | 5.39 |

EXAMPLE 6

The lipidated, dialyzed tissue factor with beta alanine of Example 1 was diluted 100-fold with a formulation buffer, which is composed of 14 mM Hepes, 60 mM sodium chloride, 2% gamma-aminobutyric acid, 4.5% L-serine, 7% sorbitol, 14 mM calcium gluconate, 0.3% BSA, 0.2% phenol, and 0.01% BHT. The formulated material was frozen at −70° C., and then thawed. The thawed material was air-dried at 20° C. and 5% relative humidity. The air-dried materials were reconstituted with water and subjected to coagulation assay by traditional prothrombin time test method.

TABLE 6

| | Clotting Times (Seconds) | | |
|---|---|---|---|
| Reagents | Level I | Level III | III/I Ratio |
| Formulated | 14.3 | 66.1 | 4.62 |
| Frozen-Thawed | 13.8 | 64.5 | 4.67 |
| Air-dried after freezing-thawing | 13.7 | 73.8 | 5.39 |

EXAMPLE 6

The lipidated, dialyzed tissue factor with beta alanine of Example 1 was diluted 100-fold with a formulation buffer, which is composed of 14 mM Hepes, 60 mM sodium chloride, 2% delta-aminovaleric acid, 4.5% L-serine, 7% sorbitol, 14 mM calcium gluconate, 0.3% BSA, 0.2% phenol, and 0.01% BHT. The formulated material was frozen at −70° C. and then thawed. The thawed material was incubated at 25 and 37° C. and assayed at weekly intervals by prothrombin time test method using a Fibrometer.

TABLE 6

| | | Clotting Times (Seconds) | | |
|---|---|---|---|---|
| Incubation days | Temp. (° C.) | Level I | Level III | III/I Ratio |
| 0 | 25 | 12.5 | 62.2 | 4.98 |
| 7 | 25 | 12.2 | 58.4 | 4.79 |
| 14 | 25 | 12.4 | 59.6 | 4.81 |
| 21 | 25 | 12.9 | 61.3 | 4.75 |
| 28 | 25 | 12.4 | 61.6 | 4.98 |
| 7 | 37 | 10.8 | 45.8 | 4.24 |
| 14 | 37 | 12.6 | 56.2 | 4.46 |
| 21 | 37 | 12.9 | 56.9 | 4.41 |
| 28 | 37 | 12.9 | 57.7 | 4.47 |

EXAMPLE 7

The lipidated, dialyzed tissue factor with beta alanine of Example 1 was diluted 100-fold with a formulation buffer, which is composed of 14 mM Hepes, 60 mM sodium chloride, 2% gamma-aminobutyric acid, 4.5% L-serine, 7% sorbitol, 14 mM calcium gluconate, 0.3% BSA, 0.2% phenol, and 0.01% BHT. The formulated material was frozen at −70° C. and then thawed. The thawed material was air-dried at 20° C. and 5% relative humidity. The air-dried materials were reconstituted with water and subjected to coagulation assay by traditional prothrombin time test method.

TABLE 7

| | Clotting Times (Seconds) | | |
|---|---|---|---|
| Reagents | Level I | Level III | III/I Ratio |
| Formulated | 14.3 | 66.1 | 4.62 |
| Frozen-Thawed | 13.8 | 64.5 | 4.67 |
| Air-dried after freezing-thawing | 13.7 | 73.8 | 5.39 |

EXAMPLE 8

The lipidated, dialyzed tissue factor with beta alanine of Example 1 was diluted 100-fold with a formulation buffer, which is composed of 14 mM Hepes, 60 M sodium chloride, 2% beta alanine, 4.5% L-serine, 7% sorbitol, 14 mM calcium gluconate, 0.3% BSA, 0.2% phenol, and 0.01% BHT. The formulated material was frozen at −70° C., and then thawed. The formulated material with freezing-thawing was air-dried at 20° C. and 5% relative humidity. The air-dried material was reconstituted with water and subjected to coagulation assay by traditional prothrombin time test method.

TABLE 8

| | Clotting Times (Seconds) | | |
|---|---|---|---|
| Reagents | Level I | Level III | III/I Ratio |
| Formulated | 14.1 | 68.5 | 4.86 |
| Frozen-Thawed | 12.9 | 57.2 | 4.43 |
| Air-dried after freezing-thawing | 13.0 | 60.0 | 4.62 |

EXAMPLE 9

The lipidated, dialyzed tissue factor with beta alanine of Example 1 was diluted 100-fold with a formulation buffer, which is composed of 14 mM Hepes, 30 mM sodium chloride, 2% beta alanine, 4.5% L-serine, 7% sorbitol, 14 mM calcium gluconate, 0.3% BSA, 0.2% phenol, and 0.01% BHT. The formulated material was frozen at −70° C., and then thawed. The formulated material with freezing-thawing was air-dried at 20° C. and 5% relative humidity. The air-dried material was reconstituted with water and subjected to coagulation assay by traditional prothrombin time test method.

TABLE 9

| | Clotting Times (Seconds) | | |
|---|---|---|---|
| Reagents | Level I | Level III | III/I Ratio |
| Formulated | 13.3 | 60.2 | 4.53 |
| Frozen-Thawed | 13.0 | 53.2 | 4.09 |
| Air-dried after freezing-thawing | 12.5 | 55.0 | 4.40 |

EXAMPLE 10

The lipidated, dialyzed tissue factor with L-alanine of Example 3 was diluted 100-fold with a formulation buffer, which is composed of 14 mM Hepes, 60 mM sodium chloride, 2% beta alanine, 4.5% L-serine, 7% sorbitol, 14 mM calcium gluconate, 0.3% BSA, 0.2% phenol, and 0.01% BHT. The formulated material was frozen at −70° C., and then thawed. The formulated material with freezing-thawing was air-dried at 20° C. and 5% relative humidity. The air-dried material was reconstituted with water and subjected to coagulation assay by traditional prothrombin time test method.

TABLE 10

| | Clotting Times (Seconds) | | |
|---|---|---|---|
| Reagents | Level I | Level III | III/I Ratio |
| Formulated | 12.4 | 55.0 | 4.44 |
| Frozen-Thawed | 12.0 | 50.0 | 4.17 |
| Air-dried after freezing-thawing | 12.0 | 53.0 | 4.42 |

EXAMPLE 11

The lipidated tissue factor was prepared as in Example 1 with the following modifications: beta alanine was replaced with glycine, and the final dialysis was conducted at 4° C. against a solution of 14 mM Hepes, 100 mM sodium chloride, 5% L-serine and 2% sorbitol, pH 7.4. The lipidated, dialyzed tissue factor was diluted 100-fold with a formulation buffer, which is composed of 14 MM Hepes, 2% beta alanine, 4.5% L-serine, 14 mM calcium gluconate, 0.3% BSA, 0.2% phenol, and 0.01% BHT, pH 7.4. The formulated material was air-dried at 20° C. in cuvets for Hemochron Jr. Signature instruments (a product of International Technidyne Corporation, Edison, N.J.). The produced cuvets with reagent were incubated at 25, 37 and 45° C. for stability studies. At weekly intervals, the cuvets were taken out of the incubators and assayed for their clotting activities. Control Level I and Level III plasma samples were added to the cuvets with the dried reagent for assay. In this assay system, reconstitution of the dried reagent is done with plasma or blood, without using water, which is different from the Fibrometer assay system. Hence, the kinetics involved in these two systems are different, as well as the clotting times. The clotting time with whole blood at day zero was 25.2 seconds.

TABLE 11

Clotting Times (Seconds)

| Incubation days | Temp. (° C.) | Level I | Level III | III/I Ratio |
|---|---|---|---|---|
| 0 | 25.2 | 20.8 | 93.8 | 4.51 |
| 7 | 25 | 21.0 | 100.5 | 4.79 |
| 14 | 25 | 20.5 | 95.8 | 4.67 |
| 21 | 25 | 20.8 | 94.7 | 4.55 |
| 7 | 37 | 22.5 | 100.3 | 4.46 |
| 14 | 37 | 23.0 | 100.5 | 4.37 |
| 21 | 37 | 21.5 | 98.3 | 4.57 |
| 7 | 45 | 21.8 | 98.0 | 4.50 |
| 14 | 45 | 22.3 | 88.5 | 3.97 |
| 21 | 45 | 22.5 | 95.0 | 4.22 |

EXAMPLE 12A

The lipidated, dialyzed tissue factor of Example 11 in 14 mM Hepes, 5% L-serine, 0.1 M sodium chloride, and 2% sorbitol, pH 7.4, was diluted 100-fold with a formulation buffer, which is composed of 14 mM Hepes, 0.15 M sodium chloride, 2% β-alanine, 4.0% sorbitol, and 1% γ-cyclodextrin, pH 7.4. γ-cyclodextrin is used to adjust the clotting time ratio of Level III and Level I plasmas. The formulated material was air-dried at 20° C. and 5% relative humidity in cuvets for Protime instrument (a product of International Technidyne Corporation, Edison, N.J.). The produced cuvets with reagent were incubated at 25, 37 and 45° C. for stability studies. At given time intervals, the cuvets were taken out of the incubators and assayed for their clotting activities. Freshly withdrawn blood, Control Level I or Level III plasma samples were added to the cuvets with the dried reagent for assay. Calcium chloride, 8.3 mM, was added to the control plasmas and loaded on the cuvet immediately for assay. In this assay system, reconstitution of the dried reagent is done with plasma or blood, without using water, which is different from Fibrometer assay system. Thence, the kinetics involved in these two systems are different, as well as the clotting times. Whole blood contains a considerable amount of red blood cells and other blood components and its clotting activity is different from that of plasma. For comparison, the clotting time with freshly withdrawn whole blood at day zero was 22.8 seconds.

TABLE 12A

Clotting Times (Seconds)

| Incubation days | Temp. (° C.) | Level I | Level III | III/I Ratio |
|---|---|---|---|---|
| 0 | — | 18.3 | 81.9 | 4.47 |
| 7 | 25 | 17.7 | 85.2 | 4.81 |
| 14 | 25 | 20.0 | 84.5 | 4.23 |
| 21 | 25 | 20.5 | 88.6 | 4.32 |
| 7 | 37 | 19.1 | 80.0 | 4.19 |
| 11 | 37 | 19.2 | 85.4 | 4.45 |
| 14 | 37 | 19.7 | 87.2 | 4.43 |
| 21 | 37 | 20.1 | 86.3 | 4.29 |

EXAMPLE 12B

Lipidated, dialyzed tissue factor of Example 11 was formulated with 100 volumes of 14 mM Hepes, 4% sorbitol and 1% β-alanine with and without polymeric carbohydrate as shown in Table 12B, air-dried and tested in the Protime Instrument System as in Example 12A. As shown in the results, γ-Cyclodextrin is a useful homogeneous polymeric carbohydrate to adjust the sensitivity of the synthetic PT reagent.

TABLE 12B

Clotting Times (Sec.)

| | Level I | Level III | III/I Ratio |
|---|---|---|---|
| No Carbohydrate | 17.3 | 70.6 | 4.1 |
| 1% Maltodextrin M-700 | 16.4 | 63.9 | 3.9 |
| 1% γ-Cyclodextrin | 17.6 | 81.8 | 4.7 |

EXAMPLE 13

The inventive amino acid stabilizer, namely 2% beta alanine in the formulation of Example 1 was replaced by other amino acids (comparative compounds) and tested for the clotting activity of the prepared reagents. Aspartic acid, arginine, glycylglycine and ε-aminocaproic acid; individually tested at the 2% (w/v) concentration level, caused a large change of Level III/I sensitivity ratio of the reagent immediately after the initial formulation or within one week of incubation at 37° C. These altered sensitivities were outside of the desired sensitivity range of 4 to 5, and these compounds were therefore judged unacceptable. The details of the results are as follows:

TABLE 13

Clotting times (Sec.)

| Amino acids | Level I | Level III | III/I Ratio |
|---|---|---|---|
| 2% Aspartic acid $H_2NCH(COOH)CH_2COOH$ | 13.6 | 33.8 | 2.49 |
| 2% Arginine $H_2NC(=NH)NHCH_2CH_2CH_2CH(NH_2)COOH$ | 32.3 | 185.4 | 5.73 |
| 2% Glycylglycine $H_2NCH_2C(=O)NHCH_2COOH$ | 12.8 | 32.2 | 2.52 |
| 2% ε-aminocaproic acid $H_2N(CH_2)_5COOH$ (after initial formulation) | 14.4 | 71.9 | 5.01 |
| 2% ε-aminocaproic acid (after 1 week at 37° C.) | 15.9 | 54.4 | 3.42 |

What is claimed is:

1. A reagent for determining prothrombin time, comprising:
   a recombinant protein tissue factor containing a portion derived from rabbit brain; an amino acid stabilizer compound selected from the group consisting of beta, gamma, and delta amino acids, and precursors thereof; and wherein the regent remains stable for at least about 2 weeks at a selected temperature without drying or lyophilization.

2. The reagent of claim 1, wherein the amino acid stabilizer compound is selected from the group consisting of beta alanine, gamma aminobutyric acid, delta aminovaleric acid, and precursors or salts thereof.

3. The reagent of claim 2, wherein the amino acid stabilizer compound is present in a concentration range of about 0.1 to 10.0% (w/v).

4. The reagent of claim 2, wherein the amino acid stabilizer compound is present in a concentration range of about 1.0 to 5.0% (w/v).

5. The reagent of claim 2, wherein the amino acid stabilizer compound is present in a concentration range of about 1.5 to 2.5% (w/v).

6. The reagent of claim 1, wherein the reagent is dried at a selected temperature and relative humidity without lyophilization and remains stable for at least about 2 weeks at a selected temperature.

7. The reagent of claim 1, wherein a portion of the recombinant protein tissue factor is derived from rabbit brain.

8. The reagent of claim 1, wherein the recombinant protein tissue factor is derived solely from rabbit brain.

9. The reagent of claim 1, wherein the reagent contains at least one synthetic phospholipid in an amount sufficient to lipidate said protein.

10. The reagent of claim 9, wherein said at least one synthetic phospholipid comprises palmitoyloleoylphosphatidylcholine or palmitoyloleoyl-phosphatidylserine.

11. The reagent of claim 10, wherein palmitoyloleoylphosphatidylcholine and palmitoyloleoylphosphatidylserine are present in a molar ratio range of about 6 to 4 to about 8 to 2 respectively.

12. The reagent of claim 1, wherein the reagent further includes a calcium compound which provides a source of calcium ions for calcium dependent coagulation factors.

13. The reagent of claim 12, wherein the calcium ions source is calcium gluconate.

14. The reagent of claim 1, wherein the reagent further includes an aldehyde free polymeric carbohydrate.

15. The reagent of claim 14, wherein the polymeric carbohydrate is gamma cyclodextrin.

16. The reagent of claim 1, wherein the reagent further includes a HEPES buffer solution having a pH in the range of about 7.0 to 7.8.

17. The reagent of claim 1, wherein the reagent has an International Sensitivity Index (ISI) of substantially 1.0.

18. The reagent of claim 1, wherein the reagent further includes an amino acid chelating agent, a carrier protein, a humectant, and a biocide.

19. The reagent of claim 18, wherein the amino acid chelating agent includes L-serine, the carrier protein includes BSA, the humectant includes sorbitol and glycerol, and the biocide includes phenol.

20. A method of preparing a reagent for determining prothrombin time, comprising the steps of:
    adding a selected amount of at least one synthetic phospholipid to a solution containing a detergent and a selected amount of an amino acid stabilizer compound selected from the group consisting of beta, gamma, and delta amino acids, and precursors thereof;
    adding a carrier protein and recombinant protein tissue factor containing a portion derived from rabbit brain to said phospholipid solution;
    incubating said protein solution for a selected time at a selected temperature to form a homogeneous mixture;
    dialyzing said homogeneous mixture in a selected dialysis medium to form lipid micelles having said tissue factor inserted therein; and
    diluting said dialyzed tissue factor with a formulation buffer;
    wherein said diluted reagent remains stable for at least about two weeks at a selected temperature.

21. The method of claim 20, wherein the amino acid stabilizer compound is selected from the group consisting of beta alanine, gamma aminobutyric acid, delta aminovaleric acid and precursors or salts thereof.

22. The method of claim 20, wherein said diluted reagent is dried at a selected temperature and relative humidity without lyophilization.

23. The method of claim 20, wherein the solution is dried in air in the temperature range of about 10 to 50° C. and a relative humidity range of about 2 to 10% relative humidity.

24. The method of claim 20, wherein a portion of the recombinant protein tissue factor is derived from rabbit brain.

25. The method of claim 20, wherein the recombinant protein tissue factor is derived solely from rabbit brain.

26. The method of claim 20, wherein said at least one synthetic phospholipid comprises palmitoyloleoylphosphatidylcholine or palmitoyloleoylphosphatidylserine.

27. The method of claim 26, wherein palmitoyloleoylphosphatidylcholine and palmitoyloleoylphosphatidylserine are present in a molar ratio range of about 6 to 4 to about 8 to 2 respectively.

28. The method of claim 20, wherein said diluted reagent includes an aldehyde free polymeric carbohydrate.

29. The method of claim 28, wherein the polymeric carbohydrate is gamma cyclodextrin.

30. The method of claim 20, wherein the detergent includes octyl glucoside.

31. The method of claim 20, wherein said reagent has an International Sensitivity Index (ISI) of substantially 1.0.

32. The method of claim 20, wherein said dialysis medium is dialyzed against a first buffer solution containing glycine and a second buffer solution containing L-serine.

33. The method of claim 20, wherein a hydrophobic resin is employed in the dialysis of the lipidated tissue factor.

34. The method of claim 20, wherein said formulation buffer comprises a buffer, a salt, an amino acid chelating agent, a humectant, a calcium compound, a carrier protein, a biocide, an antioxidant, and an amino acid stabilizer compound or a precursor thereof; and wherein the formulation buffer has a pH in the range of 7.0 to 7.8.

35. The method of claim 34, wherein the antioxidant includes butylated hydroxytoluene (BHT), the buffer includes Hepes, the salt includes sodium chloride, the amino acid chelating agent includes L-serine, and the humectant includes sorbitol and glycerol; and the carrier protein includes bovine serum albumin.

36. A method of determining the prothrombin time of a blood sample, comprising the steps of:
    reacting said blood sample with a reagent for determining prothrombin time; said reagent having a recombinant protein tissue factor containing a portion derived from rabbit brain, at least one synthetic phospholipid in an amount sufficient to activate said protein tissue factor, and an amino acid stabilizer compound selected from the group consisting of beta, gamma, and delta amino acids, and precursors thereof;

wherein the reagent has not been previously lyophilized, and remains stable for at least about two weeks at a selected temperature; and measuring the time it takes for a clot to form.

37. The method of claim 36, wherein the amino acid stabilizer compound is selected from the group consisting of beta alanine, gamma aminobutyric acid, delta aminovaleric acid, and precursors or salts thereof.

38. The method of claim 36, wherein the reagent has never been dried.

39. The method of claim 36, wherein a portion of the recombinant protein tissue factor is derived from rabbit brain.

40. The method of claim 36, wherein the recombinant protein tissue factor is derived solely from rabbit brain.

41. The method of claim 36, wherein said at least one synthetic phospholipid comprises palmitoyloleoylphosphatidylcholine or palmitoyloleoyl-phosphatidylserine.

42. The method of claim 41, wherein said palmitoyloleoylphosphatidylcholine and palmitoyloleoylphosphatidylserine are present in a molar ratio range of about 6 to 4 to about 8 to 2 respectively.

43. The method of claim 36, wherein the reagent further includes a calcium compound which provides a source of calcium ions for calcium dependent coagulation factors.

44. The method of claim 43, wherein the source of calcium ions is calcium gluconate.

45. The method of claim 36, wherein the reagent includes an aldehyde free polymeric carbohydrate.

46. The method of claim 45, wherein the polymeric carbohydrate is gamma cyclodextrin.

47. The method of claim 36, wherein the reagent has an International Sensitivity Index (ISI) of substantially 1.0.

48. The method of claim 36, wherein the reagent further includes a HEPES buffer solution having a pH in the range of about 7.0 to 7.8.

49. The method of claim 36, wherein the reagent further includes an amino acid chelating agent, a carrier protein, a humectant, and a biocide.

50. The method of claim 49, wherein the amino acid chelating agent includes L-serine, the carrier protein includes BSA, the humectant includes sorbitol and glycerol, and the biocide includes phenol.

* * * * *